(12) United States Patent
Ding et al.

(10) Patent No.: US 11,422,100 B2
(45) Date of Patent: Aug. 23, 2022

(54) COAL CONSUMPTION ONLINE MEASURING SYSTEM

(71) Applicants: China Testing & Certification International Group Co., Ltd., Beijing (CN); Nayur Technology (Beijing) Co., Ltd., Beijing (CN); Envea China Ltd., Beijing (CN)

(72) Inventors: Xinmiao Ding, Beijing (CN); Shushuang Hu, Beijing (CN); Wan Lu, Beijing (CN); Xuezhong Zhang, Beijing (CN); Xidong Yang, Beijing (CN); Yufeng Liu, Beijing (CN); Bernhard Pohle, Beijing (CN); Qianming Cao, Beijing (CN); Feng Zhang, Beijing (CN); Hongyu Liang, Beijing (CN); Jialin Jin, Beijing (CN); Junxuan Du, Beijing (CN); Fan Zhou, Beijing (CN); Lifeng Yang, Beijing (CN); Xing Shi, Beijing (CN); Daokui Cui, Beijing (CN); Weiying Liu, Beijing (CN); Dun Zhao, Beijing (CN)

(73) Assignees: CHINA TESTING & CERTIFICATION INTERNATIONAL GROUP CO., LTD., Beijing (CN); NAYUR TECHNOLOGY (BEIJING) CO., LTD., Beijing (CN); ENVEA CHINA LTD., Beijing (CN)

( * ) Notice: Subject to any disclaimer, the term of this patent is extended or adjusted under 35 U.S.C. 154(b) by 126 days.

(21) Appl. No.: 16/962,698

(22) PCT Filed: Jan. 14, 2020

(86) PCT No.: PCT/CN2020/071969
§ 371 (c)(1),
(2) Date: Jul. 16, 2020

(87) PCT Pub. No.: WO2020/211495
PCT Pub. Date: Oct. 22, 2020

(65) Prior Publication Data
US 2021/0231591 A1    Jul. 29, 2021

(30) Foreign Application Priority Data
Apr. 17, 2019    (CN) .......................... 201910309962.8

(51) Int. Cl.
*G01N 23/223*    (2006.01)
*G01N 21/35*    (2014.01)
(Continued)

(52) U.S. Cl.
CPC ............. *G01N 23/223* (2013.01); *G01F 1/66* (2013.01); *G01F 1/74* (2013.01); *G01F 1/86* (2013.01);
(Continued)

(58) Field of Classification Search
CPC .... G01F 1/66; G01F 1/74; G01F 1/86; G01N 9/24; G01N 21/3563; G01N 21/65;
(Continued)

(56) References Cited

U.S. PATENT DOCUMENTS

| | | |
|---|---|---|
| 6,137,294 A | 10/2000 | Best et al. |
| 2007/0092060 A1 | 4/2007 | Grodzins |
| 2007/0184556 A1* | 8/2007 | Wang ..................... F22B 33/18 436/143 |

FOREIGN PATENT DOCUMENTS

| | | |
|---|---|---|
| CN | 2570778 Y | 9/2003 |
| CN | 101283268 A | 10/2008 |

(Continued)

OTHER PUBLICATIONS

International Search Report and Written Opinion with concise English translation regarding PCT/CN2020/071969 dated Apr. 1, 2020, 11 pages.

(Continued)

*Primary Examiner* — Mark R Gaworecki
(74) *Attorney, Agent, or Firm* — Crowell & Moring LLP

(57) ABSTRACT

The present application discloses a coal consumption online measuring system, which belongs to the field of analysis and measurement technology. The system includes an equivalent atomic number measuring device, a flow rate measuring device, an ash content measuring device, a volatile content measuring device, a moisture content measuring device and a data acquisition and processing device. The data acquisition and processing device iteratively corrects the measured real-time density, real-time ash content, real-time moisture content and/or real-time volatile content; and the data acquisition and processing device performs online calculation of the coal consumption according to a real-time volume flow rate and the iteratively-corrected real-time density, real-time ash content, real-time moisture content and real-time volatile content. The coal consumption online measuring system is an independent and complete working system which only uses the measured data from the coal consumption online measuring system itself to obtain the final required results.

9 Claims, 2 Drawing Sheets

(51) Int. Cl.

| | | |
|---|---|---|
| *G01N 21/65* | (2006.01) | |
| *G01N 33/22* | (2006.01) | |
| *G01N 21/85* | (2006.01) | |
| *G01F 1/66* | (2022.01) | |
| *G01F 1/86* | (2006.01) | |
| *G01N 9/24* | (2006.01) | |
| *G01N 21/3563* | (2014.01) | |
| *G01F 1/74* | (2006.01) | |
| *G01N 23/04* | (2018.01) | |

(52) U.S. Cl.
CPC .......... *G01N 9/24* (2013.01); *G01N 21/3563* (2013.01); *G01N 21/65* (2013.01); *G01N 21/85* (2013.01); *G01N 33/222* (2013.01); G01N 23/04 (2013.01); G01N 2223/07 (2013.01); G01N 2223/507 (2013.01)

(58) Field of Classification Search
CPC ...... G01N 21/85; G01N 23/04; G01N 23/223; G01N 33/222; G01N 2223/07; G01N 2223/507
See application file for complete search history.

(56) References Cited

FOREIGN PATENT DOCUMENTS

| | | | |
|---|---|---|---|
| CN | 101446418 | A | 4/2009 |
| CN | 201653849 | U | 11/2010 |
| CN | 102749345 | A | 10/2012 |
| CN | 103375808 | A | 10/2013 |
| CN | 104198503 | A | 12/2014 |
| CN | 104596792 | A | 5/2015 |
| CN | 105807029 | A | 7/2016 |
| CN | 106896119 | A | 6/2017 |
| CN | 110133007 | A | 10/2019 |

OTHER PUBLICATIONS

First Office Action regarding CN201910309962.8 dated Oct. 30, 2013, 10 pages.
Notice of Allowance regarding CN201910309962.8 dated Dec. 12, 2019, 3 pages.
Li U et al., "Analysis of Difficulties in Online Calculation of Coal Consumption," vol. 22 No. 7, Jul. 2009, 4 pages.
C. Cierpisz et al., "Experiences with On-Line Microwave Moisture Monitoring Systems for Coal," Buenos Aires, Argentina, 1989, 7 pages.

* cited by examiner

COAL CONSUMPTION ONLINE MEASURING SYSTEM

TECHNICAL FIELD

The present application relates to the field of analysis and measurement technology, and specially relates to a coal consumption online measuring system.

BACKGROUND TECHNOLOGY

Coal is an important part of China's industrial energy structure, and is widely used in many industries. Particularly, coal is the main energy source of thermal power plants and cement production plants and is the main raw material of the coal chemical industry. The exact amount of coal (calorific value) consumed by various industries and energy consumption enterprises is an important basis for formulating a national energy strategy, as well as being the basic data for calculation and verification of enterprise carbon emission. In order to ensure that government departments can accurately determine the national coal consumption amount, NDRC (National Development and Reform Commission) and AQSIQ (Administration of Quality Supervision, Inspection and Quarantine) jointly formulated and issued a notice of "Promotion and construction scheme of energy consumption online measuring systems for key energy consumption plants" in 2017. Coal consumption is one part of energy consumption, and the measuring of coal consumption is particularly complex.

Coal consumption=calorific value (of coal)*coal mass. Because coal is naturally formed and there are great diversities in calorific values of coals from different places of origin and different batches, energy consumption statistics vary greatly. Therefore, the detection and measuring of coal consumption, especially on-line measuring, has always been a technical challenge. It needs to be noted that, coal is mined in blocks, and in order to achieve sufficient and uniform combustion, coal blocks need to be pre-ground into fine coal powder during industrial production. In the description hereinafter, the measuring object is coal powder.

There are usually two ways to measure calorific value:

One way is to burn unit mass of coal powder in laboratory, then measure the temperature rise of the heated medium, and calculate the calorific value.

The other way is calculation by a coal calorific value formula, which needs to measure the characteristic parameters of ash content, volatile content, moisture content and ash element content of coal powder. Taking bituminous coal used in clinker calcination of the cement industry as an example, the specific calorific value calculation formula is as follows:

$$Q_{net.ad} = 8575.63 - 17.63 V_{ad} - 94.64 A_{ad} - 167.89 M_{ad} + 41.52 CRC$$

Wherein, $Q_{net.ad}$ is the calorific value of coal, in unit: Cal/g, kcal/kg, $V_{ad}$ is air-dried basis volatile content of coal, in unit: % (hereinafter referred to as volatile content), $A_{ad}$ is air-dried basis ash content of coal, in unit: % (hereinafter referred to as ash content), $M_{ad}$ is air-dried basis moisture content of coal, in unit: % (hereinafter referred to as moisture content), CRC is Char Residue Characteristic of bituminous coal (value of 1-8, depending on the element composition and element contents of the ash).

Coal powder mass is normally measured in its milling stage or transporting stage. In the milling stage, a weight sensor of the coal-feeding device is used for measuring the coal mass. According to the production task of the coal consumption enterprise, a conveyor belt apparatus or a gas pipeline transporting apparatus may be used in the coal powder transporting stage. The conveyor belt apparatus may use a coal powder transporting belt scale system; the gas pipeline transporting apparatus transports coal powder by gas-solid two-phase transporting technology using air to transport solid particles, wherein the measuring of coal powder mass is by utilizing technology such as microwave to measure the volume flow rate of coal powder in pipelines and then calibrating the density characteristic of the coal powder so as to determine the mass flow rate thereof. Mass=volume*density.

Corresponding to the methods for determining calorific value and mass of coal powder, there are also many methods for measuring coal consumption in actual production and engineering. The representative methods are as follows:

Method 1: Traditional Offline Statistics Method.

That is, coal samples are collected in the field manually or by automated devices, and then the calorific value of the coal are determined by a coal calorific value measuring equipment in laboratory utilizing the principle of temperature rise. The coal mass is measured by a coal powder transporting belt scale system or a weight sensor of the coal-feeding device used in the production line of the enterprise. Because the sampling measurement needs a certain period, coal is generally sampled every day or every batch, for example, in a cement clinker production enterprise. The formula "Energy consumption=calorific value (of coal)*coal mass" is used to determine the coal consumption value of the current day or the current batch.

When measuring the calorific value, this method would cause a large error of the measured calorific value, because of insufficient representation of the coal powder sampling. Moreover, the long sampling and measuring period would result in poor timeliness, so it is unable to direct or adjust the energy consumption status in time.

Additionally, the measuring process of coal powder mass depends on the reliability of the coal powder weighing device, so the measured results are unstable, unverifiable and have many human factors, and sometimes the results are just not credible. As the acquisition of coal powder mass relies on the production line device of the enterprise, the measuring system is not independent.

Method 2: Incomplete Online Statistics Method.

The calorific value is calculated by using the calorific value calculation formula, the real-time mass flow rate is measured by an on-line mass measuring device, and the coal consumption within a prescribed time period is calculated by integration.

Calorific value calculation requires to measure the ash content, volatile content, moisture content of coal powder and determine the Char Residue Characteristic value according to the element composition of ash and the content of sulfur element. This method normally use a gamma-ray ash detector (ash content measuring device) to measure the total ash content, a moisture content measuring device to measure the moisture content, and a volatile content measuring device to measure the volatile content. There are already on-line ash measuring devices and on-line moisture measuring devices, but there is no readily-applicable online application product for measuring the volatile content of coal powder. And because there is also no online product for measuring the element composition of ash and the content of sulfur element, the Char Residue Characteristic value cannot be determined online in real time. Therefore, as the calorific value calculation is not completely online, this method would have a large error.

Additionally, most of the existing on-line mass flow rate measuring devices measure the volume flow rate of coal powder in the gas-solid two-phase transporting pipeline, and then calibrate the density characteristic of the coal powder so as to determine the mass flow rate thereof. Its accuracy relies on the calibration of coal powder (density). The procedure of calibration is relatively complex and relies on the way of "weight measuring by a coal transporting belt scale system or a weight sensor of the coal-feeding device" used in Method 1. Additionally, when calibration has been completed, the density of the coal powder may change when the quality of the coal powder changes, so that the calculated mass flow rate would deviate from the correct value. In other words, its volume is measured online and relatively accurate, but its density is only the data of the coal sample used for calibration, which is a fixed value and does not change online in real time along with the coal quality. Therefore, the calculated mass flow rate would have deviations.

Overall, the disadvantages of this method are: 1) the calorific value measuring is not completely online; 2) the mass flow rate data is strongly relying on the calibration, and the calibration procedure is complex. 3) during the production, because density change would be caused by quality change of the coal powder and density calibration cannot be carried out immediately, thus, the results are not accurate; 4) the ash element is not measured online, and thus the mass flow rate cannot be corrected accordingly.

The patent literature "CN 103375808 A" relates to this method. From the patent literature, it can be seen that 1) coal powder sample is needed for calibration in order to obtain the parameters of ash content, moisture content and volatile content to calculate the calorific value; 2) Online mass weighing by the radiation source device is actually not practical, because it's based on the principle that the radiation ray passes through the coal-powder layer on the coal conveyor belt and its attenuation can be measured to calculate the transported amount of coal powder, however, the thickness of coal powder cannot be kept consistent in the belt width direction, so the acquired attenuation data is not accurate, and in fact, no such equipment or product has been applied in practice as described in this patent literature; 3) no on-line measuring of ash element is performed, and thus the mass flow rate cannot be corrected accordingly; 4) the influence of Char Residue Characteristic on calculation of the calorific value is ignored; and 5) the main purpose of the technology of this patent literature is to control the coal powder combustion in the boiler rather than measuring parameters, so the accuracy thereof is not high.

The common disadvantages of the above-mentioned methods, including other coal consumption measuring methods that use multiple ways in combination, are: Firstly, during the coal consumption measuring or calculation process, data from equipment of the energy consumption plant is needed to participate in the calculation thereof or directly serve as an intermediate measuring result, so it is not a complete and independent online measuring system and is thus easily disturbed by human factors which adversely affects the objectivity and accuracy of the measured results. Secondly, the existing on-line coal consumption measuring methods need to perform a lot of tedious field calibration work, and once a relatively large change happens to the category or the quality of the coal used, the system needs to be re-calibrated, otherwise the accuracy thereof would seriously deviate. Thirdly, in the existing measuring method, since the contents of the respective elements in the ash are not measured online, the measuring or calculation process thereof is only a one-direction procedure, with no correction of the output results of the measuring process, so it is not a closed-loop calculation.

SUMMARY OF THE INVENTION

To solve the above technical problems, the present application provides a coal consumption online measuring system, the coal consumption online measuring system of the present application is an independent and complete working system which only uses the measured data from the coal consumption online measuring system itself and does not need to use any data from any production equipment of the energy consumption plant to participate in the calculation thereof or directly serve as an intermediate measuring result, so that the system is not easily disturbed by human factors, and a complete and independent on-line real-time measuring of coal consumption is realized, with accurate measuring results.

The technical solution provided by the present application is as follows:

The coal consumption online measuring system comprises a solid particle equivalent atomic number measuring device, a gas-solid two-phase flow rate measuring device, an ash content measuring device, a volatile content measuring device and a moisture content measuring device. The solid particle equivalent atomic number measuring device and the gas-solid two-phase flow rate measuring device are installed on a coal transporting pipeline of a coal transporting path, the ash content measuring device, the volatile content measuring device and the moisture content measuring device are arranged on the coal transporting path, the solid particle equivalent atomic number measuring device, the gas-solid two-phase flow rate measuring device, the ash content measuring device, the volatile content measuring device and the moisture content measuring device are all connected to a data acquisition and processing device, wherein:

The solid particle equivalent atomic number measuring device and the gas-solid two-phase flow rate measuring device are configured to measure a real-time density and a real-time volume flow rate of coal powder in the coal transporting pipeline. The ash content measuring device, the volatile content measuring device and the moisture content measuring device are configured to measure a real-time ash content, a real-time moisture content and a real-time volatile content of coal powder on coal transporting path, the real-time ash content includes a total content of ash, the element composition of the ash and the contents of the respective elements in the ash;

The data acquisition and processing device is configured to calculate a matrix characteristic of the coal powder according to one or more of the measured real-time density, real-time ash content, real-time moisture content and real-time volatile content, and iteratively correct one or more of the measured real-time density, real-time ash content, real-time moisture content and real-time volatile content according to the calculated matrix characteristic of the coal powder;

The data acquisition and processing device is configured to calculate a real-time mass flow rate according to the iteratively-corrected real-time density and the real-time volume flow rate, and calculate a real-time calorific value of the coal powder according to the iteratively-corrected real-time ash content, real-time moisture content and real-time volatile content;

The data acquisition and processing device is configured to calculate a real-time energy of the coal powder according to the real-time mass flow rate and the real-time calorific value, and perform time integration of the real-time energy to determine a coal consumption within a prescribed time period.

Further, the solid particle equivalent atomic number measuring device comprises a radiation source device, a detection device and a first analysis and communication component; The radiation source device is configured to emit radiation rays towards the coal powder in the coal transporting pipeline, the detection device is configured to receive a signal after the radiation rays penetrate the coal powder or are reflected from the coal powder, the first analysis and communication component is configured to analyze and obtain an equivalent atomic number of the coal powder in the coal transporting pipeline, calculate the real-time density according to the equivalent atomic number and send the real-time density to the data acquisition and processing device. The radiation source device is an X-ray source or a γ-ray source Further, the gas-solid two-phase flow rate measuring device comprises at least one set of microwave emitting unit and microwave receiving unit distributed on the coal transporting pipeline, the microwave emitting unit and the microwave receiving unit are both connected to a second analysis and communication component. The microwave emitting unit is configured to emit microwaves and the microwave receiving unit is configured to receive the microwaves reflected by the coal powder in the coal transporting pipeline, the second analysis and communication component is configured to analyze and obtain the real-time volume flow rate in the coal transporting pipeline and send the real-time volume flow rate to the data acquisition and processing device.

Further, the ash content measuring device is arranged on the coal transporting pipeline, and the ash content measuring device is an X-ray fluorescence spectral element analysis device. The X-ray fluorescence spectral element analysis device comprises an X-ray generating device, an X-ray detector component, an optical path device, a first sampling device and a third analysis and communication component; The first sampling device is configured to grab a first coal powder sample from inside the coal transporting pipeline and transport the first coal powder sample to a working area of the X-ray generating device, the X-ray generating device is configured to emit X-rays which pass through the optical path device and irradiate the first coal powder sample to produce reflected X-rays with information on the elements in the coal powder, the X-ray detector component is configured to receive the reflected X-rays and the third analysis and communication component is configured to analyze and process the reflected X-rays to determine the total content of ash in the first coal powder sample, the element composition of the ash and the contents of the respective elements in the ash and send the determined parameters to the data acquisition and processing device.

Further, the volatile content measuring device and the moisture measuring device are arranged on the coal transporting pipeline, the volatile content measuring device and the moisture content measuring device are integrated in one structure which comprises a light source component, a detector component, a second sampling device and a fourth analysis and communication component; The second sampling device is configured to grab a second coal powder sample from the coal transporting pipeline and transport the second coal powder sample to a working area of the light source component. The light source component is configured to emit light to illuminate the second coal powder sample to produce reflected or transmitted light with information on the volatile content and moisture content of the coal powder. The detection component is configured to collect the reflected or transmitted light and the fourth analysis and communication component is configured to analyze and process the reflected or transmitted light to determine the volatile content and moisture content of the second coal powder sample and then send the determined parameters to the data collection and processing device; The light source component is an infrared light source or a Raman light source.

Further, the first sampling device and the second sampling device are the same sampling device, the first coal powder sample and the second coal powder sample are the same coal powder sample.

Further, the coal consumption online measuring system is used in a production line of a coal consumption plant, the production line includes one or more coal transporting pipelines. When multiple coal transporting pipelines are included:

each of the coal transporting pipelines is provided with a corresponding solid particle equivalent atomic number measuring device, a corresponding gas-solid two-phase flow rate measuring device, a corresponding ash content measuring device, a corresponding volatile content measuring device and a corresponding moisture content measuring device;

each of the coal transporting pipelines is provided with a solid particle equivalent atomic number measuring device and a gas-solid two-phase flow rate measuring device, and one set of ash content measuring device, volatile content measuring device and moisture content measuring device is provided for a subgroup of coal transporting pipelines using coal powder of the same quality among the multiple coal transporting pipelines. The set of ash content measuring device, volatile content measuring device and moisture content measuring device is arranged on a common coal transporting path corresponding to the subgroup of coal transporting pipelines using coal powder of the same quality.

Further, the solid particle equivalent atomic number measuring device and the gas-solid two-phase flow rate measuring device are located upstream of the ash content measuring device, the volatile measuring content device and the moisture content measuring device in the coal transporting direction of the coal transporting pipeline.

Further, the solid particle equivalent atomic number measuring device, the gas-solid two-phase flow rate measuring device, the ash content measuring device, the volatile content measuring device and the moisture content measuring device are located on a vertical part of the coal transporting pipeline.

The present application has the following beneficial effects:

The coal consumption online measuring system of the present application is an independent and complete working system, in the coal consumption measuring or calculation process, the system only uses the data measured by itself, so it has no influence on the existing production process of the energy consumption plant, and does not need any data from any production equipment of the energy consumption plant to participate in the calculation thereof or directly serve as an intermediate measuring result, and thus the result thereof would not be interfered with by human factors, that is to say, the present application is a complete and completely independent online measuring system and is not easily disturbed by human factors which adversely affect the objectivity and accuracy of the measured results. In the coal consumption online measuring system provided by the present application, each data is acquired online or in real time, and thus the statistical result is also a completely online result, thereby realizing online real-time measuring of coal consumption. The system does not need a lot of tedious field calibration, and the installation and operation thereof are simple. During the production process, when the quality of coal powder changes, the system can automatically match parameters, so the statistical results are accurate. The system can also carry out iterative correction calculation according to the data to correct any measuring error caused by any change of the quality of the coal powder, so the measuring results would be more accurate.

DETAILED DESCRIPTION OF SPECIFIC EMBODIMENTS

In order to render the technical problems to be solved by the present application and the technical solutions and advantages thereof more clear, hereinafter, detailed description will be given in conjunction with the appended drawings and specific embodiments.

Figure 1:
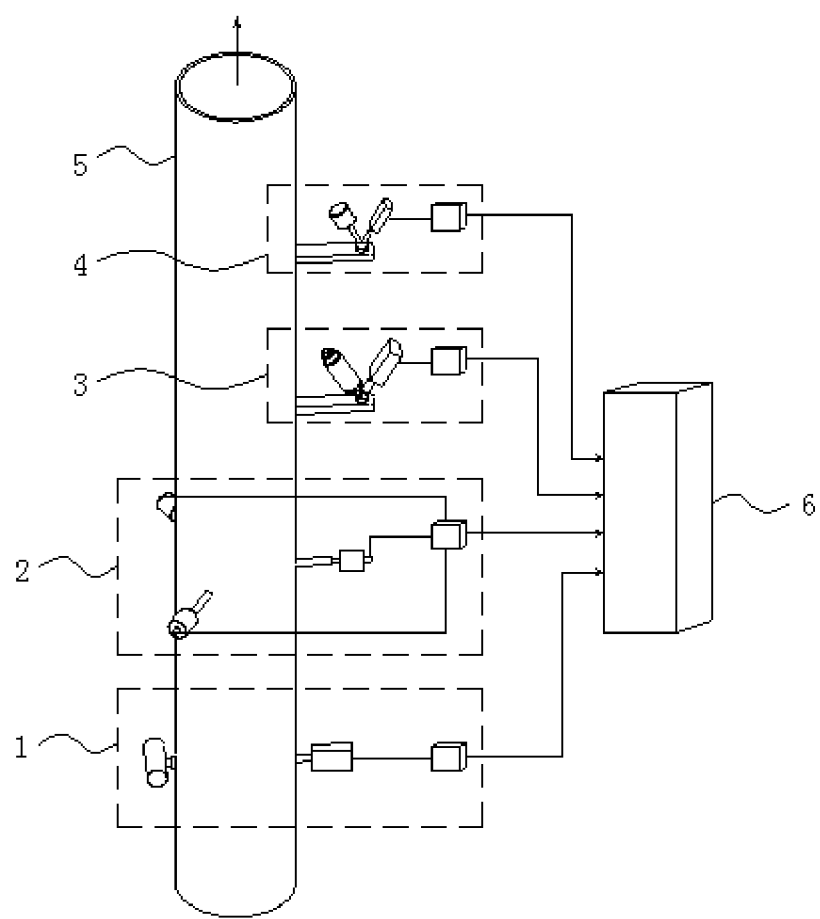
FIG. 1 is a schematic diagram of the coal consumption online measuring system of the present application.
Figure 2:
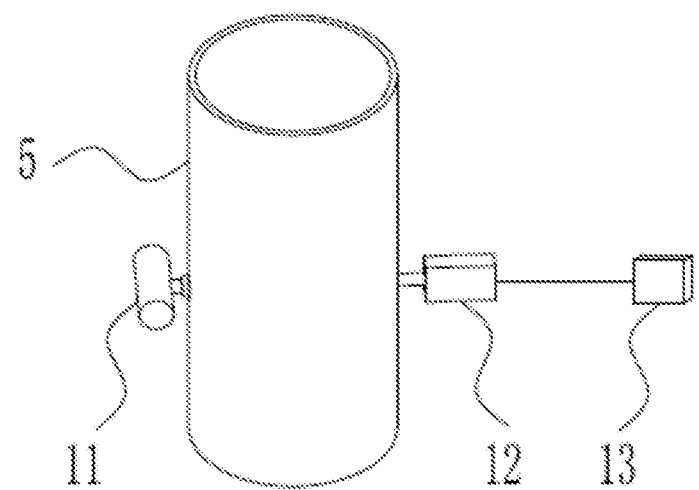
FIG. 2 is a schematic diagram of the solid particle equivalent atomic number measuring device.
Figure 3:
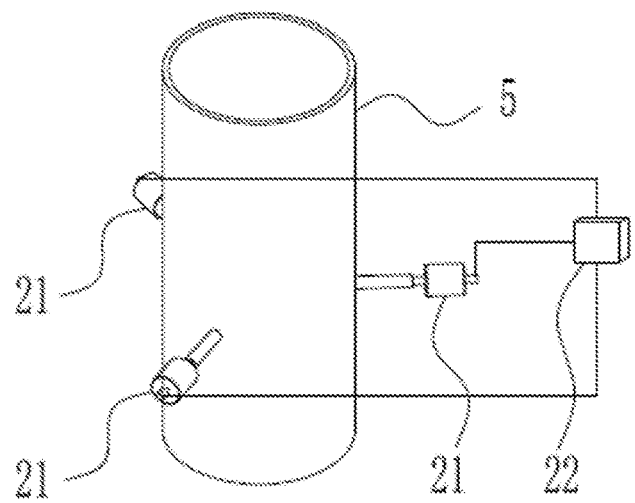
FIG. 3 is a schematic diagram of the gas-solid two-phase flow rate measuring device.

The present application provides a coal consumption on-line measuring system, as shown in FIG. 1, the system comprises a solid particle equivalent atomic number measuring device 1, a gas-solid two-phase flow rate measuring device 2, an ash content measuring device 3, a volatile content measuring device 4 and a moisture content measuring device 4. The solid particle equivalent atomic number measuring device 1 and the gas-solid two-phase flow rate measuring device 2 are arranged on the coal transporting pipeline 5 of the coal transporting path. The ash content measuring device 3, the volatile content measuring device 4 and the moisture content measuring device 4 are arranged on the coal transporting path.

In the present application, the coal blocks are milled into coal powder in a coal mill, then, the coal powder is pneumatically transported from the coal powder bunker into the coal transporting pipeline in the form of gas-solid two-phase by a conveyor, and finally enters the combustion chamber to be combusted. The coal transporting path refers to the path composed of the coal mill, the coal powder bunker, the conveyor and the coal transporting pipeline.

The solid particle equivalent atomic number measuring device and the gas-solid two-phase flow rate measuring device perform measuring on the coal powder mass that is eventually actually combusted, so the solid particle equivalent atomic number measuring device and the gas-solid two-phase flow rate measuring device need to be arranged on the coal transporting pipeline. The ash content measuring device, the volatile content measuring device and the moisture content measuring device measure the ash content, moisture content and volatile content of the coal powder, which are inherent characteristics of the coal powder and can be measured anywhere in the coal transporting path. The ash content measuring device, the volatile content measuring device and the moisture content measuring device can be arranged at any location on the coal transporting path which is not limited to the coal transporting pipeline.

The solid particle equivalent atomic number measuring device 1, the gas-solid two-phase flow rate measuring device 2, the ash content measuring device 3, the volatile content measuring device 4 and the moisture content measuring device 4 are all connected to a data acquisition and processing device 6, wherein:

The solid particle equivalent atomic number measuring device 1 and the gas-solid two-phase flow rate measuring device 2 measure a real-time density and a real-time volume flow rate of coal powder in the coal transporting pipeline 5. The ash content measuring device 3, the volatile content measuring device 4 and the moisture content measuring device 4 measure a real-time ash content, a real-time moisture content, and a real-time volatile content of coal powder in the coal transporting path. The real-time ash content includes a total ash content, the element composition of the ash and the contents of the respective elements in the ash.

When installing the present application, only necessary measuring holes and fixing devices are added to the corresponding locations on the coal transporting path. The measured real-time density, real-time volume flow rate, real-time ash content, real-time moisture content and real-time volatile content are sent to the data acquisition and processing device 6. The data acquisition and processing device 6 processes the data given by each sub device in real time, calculates the required data of instantaneous mass flow rate and real-time calorific value, and thus determines the statistical results of coal consumption. In addition, the present application can carry out iterative correction calculations of each data by utilizing an established mathematic model.

The data acquisition and processing device 6 calculate a matrix characteristic of the coal powder according to one or more of the measured real-time density, real-time ash content, real-time moisture content and real-time volatile content, and iteratively correct one or more of the measured real-time density, real-time ash content, real-time moisture content and real-time volatile content according to the calculated matrix characteristic of the coal powder.

When measuring each parameter of the coal powder, the measured results are affected by change of matrix of the coal powder sample. The change of matrix of the coal powder sample to be measured refers to the change of its constituent elements and the change of the contents of the respective elements. Taking X-ray measurement of the ash content as an example, the change of matrix directly affects the measuring of the characteristic X-ray intensity of the elements to be measured. With the same content of an element to be measured in two samples, the measured characteristic X-ray intensity thereof would be different due to difference in the matrices thereof. Hence, the matrix characteristic is one important error source of the measuring.

The present application calculates the matrix characteristic of the coal powder from the respective measured parameters, and then iteratively corrects the respective measured parameters according to the calculated matrix characteristic of the coal powder, thereby correcting any measurement error caused by change of quality of the coal powder.

The data acquisition and processing device 6 calculates a real-time mass flow rate $M_t$ according to the iteratively-corrected real-time density $\rho_t$ and real-time volume flow rate $V_t$, $M_t=\rho_t*V_t$. Since the coal powder density data is given by the solid particle equivalent atomic number measuring device 1, it is not necessary to calibrate the on-line gas-solid two-phase flow rate measuring device 2, so that on-line mass flow rate detection is completely realized.

The data acquisition and processing unit 6 calculates a real-time calorific value of the coal powder according to the iteratively-corrected real-time ash content, moisture content, and volatile content.

There are different calculation formulas for different kinds of coal powders. Taking bituminous coal used in clinker calcination of the cement industry as an example, the calorific value calculation model thereof is as follows:

$$Q_{net.ad}=8575.63-17.63V_{ad}-94.64A_{ad}-167.89M_{ad}+41.52CRC$$

Wherein, $Q_{net.ad}$ is the calorific value of coal,
$V_{ad}$ is air-dried basis volatile content of coal,
$A_{ad}$ is air-dried basis total ash content of coal,
$M_{ad}$ is air-dried basis moisture content of coal, in unit: %
CRC is Char Residue Characteristic of bituminous coal, which has a value of 1-8 depending on the element composition and element contents of the ash.

It should be pointed out that, although different coal powders have different calculation formulas, the required parameters for the calculation thereof are consistent. The data measured by the present system is enough to fulfill the calorific value calculation of different kinds of coal powders.

The data acquisition and processing device 6 calculates a real-time energy $Q_t$ of the coal powder according to the real-time mass flow rate $M_t$ and the real-time calorific value $Q_{net.ad}$, $Q_t=M_t*Q_{net.ad}$. The data acquisition and processing device 6 performs time integration on the real-time energy $Q_t$ to determine a coal consumption Q within a prescribed time period, $Q=\int Q_t$.

The coal consumption online measuring system of the present application is an independent and complete working system, in the coal consumption measuring or calculation process, the system only uses the data measured by itself, so it has no influence on the existing production process of the energy consumption plant, and does not need any data from any production equipment of the energy consumption plant to participate in the calculation thereof or directly serve as an intermediate measuring result, and thus the result thereof would not be interfered with by human factors, that is to say, the present application is a complete and completely independent online measuring system and is not easily disturbed by human factors which adversely affect the objectivity and accuracy of the measured results. In the coal consumption online measuring system provided by the present application, each data is acquired online or in real time, and thus the statistical result is also a completely online result, thereby realizing online real-time measuring of coal consumption. The system does not need a lot of tedious field calibration, and the installation and operation thereof are simple. During the production process, when the quality of coal powder changes, the system can automatically match parameters, so the statistical results are accurate. The system can also carry out iterative correction calculation according to the data to correct any measuring error caused by any change of the quality of the coal powder, so the measuring results would be more accurate.

In the present application, the solid particle equivalent atomic number measuring device can be a radiation-type measuring device, and as one of the preferred embodiments, the solid particle equivalent atomic number measuring device 1 comprises a radiation source device 11, a detection device 12 and a first analysis and communication component 13; the radiation source device 11 emits radiation rays towards the coal powder in the coal transporting pipeline 5, and the detection device 12 receives a signal after the radiation rays penetrate the coal powder or are reflected from the coal powder. The first analysis and communication component 13 analyzes and obtains the equivalent atomic number of the coal powder in the coal transporting pipeline, calculates a real-time density according to the equivalent atomic number, and send the real-time density to the data acquisition and processing device 6; The radiation source device 11 could be an X-ray source and a γ-ray source, but an X-ray source is preferred.

In the present application, the gas-solid two-phase flow rate measuring device can be a microwave measuring device, and as one of the preferred embodiments, the gas-solid two-phase flow rate measuring device 2 comprises at least one set of microwave emitting unit and microwave receiving unit distributed on the coal transporting pipeline 5. Preferably, the microwave emitting unit and the microwave receiving unit can be an integrated microwave emitting and receiving unit (21) which is connected to a second analysis and communication component 22. The integrated microwave emitting and receiving unit 21 emits microwaves and receives the microwave reflected by the coal powder in the coal transporting pipeline 5. The second analysis and communication component 22 obtains a real-time volume flow rate in the coal transporting pipeline according to the analysis of the received signal, and sends the real-time volume flow rate to the data acquisition and processing device 6.

Specifically, the second analysis and communication component analyzes the energy information and spectrum information of the received microwave signal. The energy information represents the particle size of the coal powder, and the spectrum information represents the flow velocity of the coal powder. The real-time volume flow rate of the coal powder can be determined through the energy information and spectrum information.

Preferably, multiple integrated microwave emitting and receiving units are included, such as 3 such units. The multiple units are regularly distributed on the wall of the coal transporting pipeline, and individually perform microwave measurement on the coal powder passing through the coal transporting pipeline. The purpose is to improve the accuracy of measurement and reduce any error caused by uneven distribution of coal powder in the pipeline.

The above indicates that the ash content measuring device, the volatile content measuring device and the moisture content measuring device can be arranged at any location on the coal transporting path. A preferred embodiment of the structure and installation location of the ash content measuring device, the volatile content measuring device and the moisture content measuring device are given here:

The ash content measuring device of the present application is preferably arranged on the coal transporting pipeline 5. The ash content measuring device 3 can be an X-ray fluorescence spectral element analysis device, and as one of the preferred embodiments, the X-ray fluorescence spectral element analysis device comprises an X-ray generating device 31, an X-ray detector component 32, an optical path device 33, a first sampling device 34 and a third analysis and communication component 35.

When the X-ray fluorescence spectrum element analysis device is working, the first sampling device 34 grabs coal powder from inside the coal transporting pipeline 5, forms a first coal powder sample 36 and transports it to a working area of the X-ray generation device 31. The X-ray generation device 31 emits X-rays which pass through the optical path device 33 and irradiate the first coal powder sample 36 to produce reflected X-rays with information on the elements in the coal powder. The X-ray detector component 32 receives the reflected X-rays and the third analysis and communication component 35, analyzes and processes the reflected X-rays to determine the total ash content, the element composition of the ash and the contents of the respective elements in the ash and sent the determined parameters to the data acquisition and processing device 6.

The optical path device 33 is a well-known configuration of an X-ray fluorescence spectral element analysis device 3, the purpose thereof is to achieve more accurate results by configuring different optical path performances for different elements.

In the present application, the ash content measuring device is arranged on the coal transporting pipeline to measure the real-time ash content of the coal powder at the coal transporting pipeline. Because the real-time ash content measured at the coal transporting pipeline is more sensitive to any change of quality of the coal powder, the result can be made more accurate.

In the present application, the volatile content measuring device and the moisture measuring device is preferably arranged on the coal transporting pipeline 5. The volatile content measuring device and the moisture content measuring device can be light spectral analysis devices. As one of the preferred embodiments, the volatile content measuring device and the moisture content measuring device can be integrated in one structure 4 which comprises a light source component 41, a detector component 42, a second sampling device 43 and a fourth analysis and communication component 44; The second sampling device 43 grabs coal powder from inside the coal transporting pipeline 5, forms a second coal powder sample 45 and transports it to a working area of the light source component 41. The light source component 41 emits light to illuminate the second coal powder sample 45 to produce reflected or transmitted light with information on the volatile content and moisture content of the coal powder. The detection component 42 collects the reflected or transmitted light and the fourth analysis and communication component 44 analyzes and processes the reflected or transmitted light to determine the volatile content and moisture content of the second coal powder sample 45 and send the determined parameters to the data collection and processing device 6. The light source component 41 can be an infrared light source or a Raman light source. An infrared light source component is preferred, and the corresponding detector component is an infrared detector component.

In the present application, the volatile content measuring device and the moisture content measuring device are arranged on the coal transporting pipeline to measure the real-time volatile content and moisture content of the coal powder at the coal transporting pipeline. Because the real-time volatile content and moisture content measured at the coal transporting pipeline are more sensitive to any change of quality of the coal powder, the results can be made more accurate.

In the present application, the X-ray fluorescence spectral element analysis device and the integrated volatile content and moisture content measurement system can also share one set of sampling device, and the formed coal powder sample can also be shared. At this point, the first sampling device and the second sampling device can be the same sampling device, and the first coal powder sample and the second coal powder sample can be the same coal powder sample, so as to reduce duplicated structures and costs.

Figure 4:
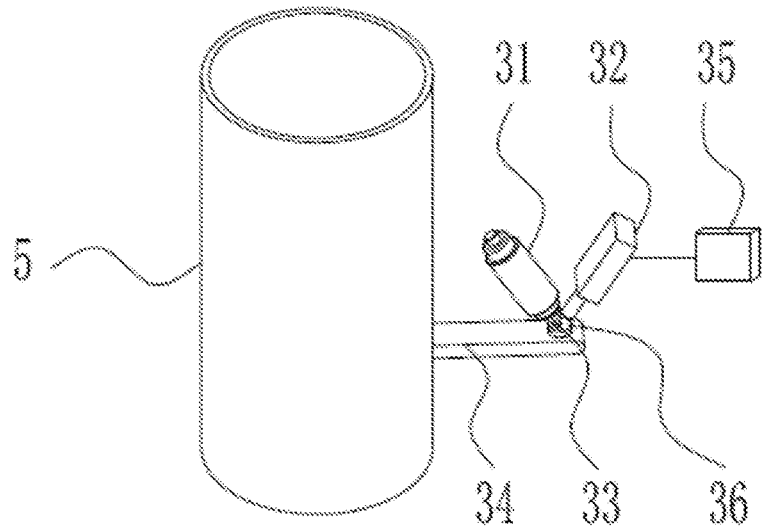
FIG. 4 is a schematic diagram of the ash content measuring device
Figure 5:
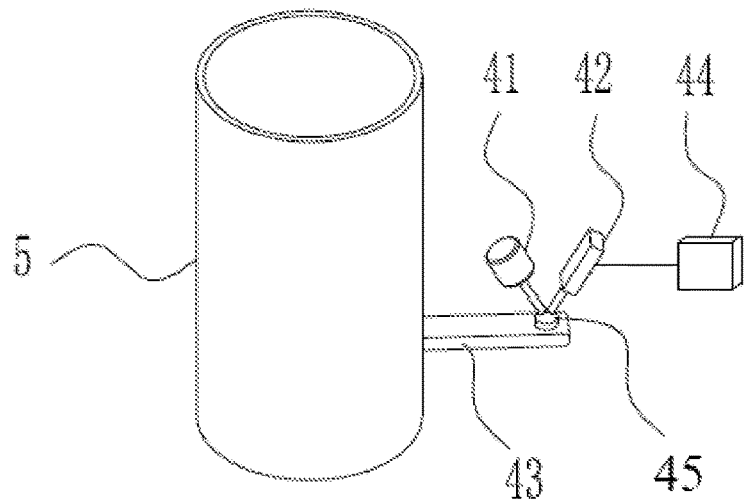
FIG. 5 is a schematic diagram of the volatile content and moisture content measuring device.

The afore-mentioned ash content measuring device, volatile content measuring device and moisture content measuring device being arranged on the coal transporting pipeline refers to that the sampling device(s) thereof samples the coal powder at the coal transporting pipeline, and is not intended to limit that the ash content measuring device, volatile content measuring device and moisture content measuring device must be positioned on the coal transporting pipeline. Because the coal powder in the coal transporting pipeline just needs to be sampled and measured, the ash content measuring device, volatile content measuring device and moisture content measuring device may not be positioned on the coal transporting pipeline, and it is only required that the sampling devices take samples from the coal transporting pipeline and send them to the ash content measuring device, volatile content measuring device and moisture content measuring device. Of course, the ash content measuring device, the volatile content measuring device and the moisture content measuring device can also be positioned on the coal transporting pipeline, as in the embodiments shown in FIG. 1, FIG. 4 and FIG. 5.

The coal consumption online measuring system is used in a production line of a coal consumption plant, the production line includes one or more coal transporting pipelines. If there is only one coal transporting pipeline in the production line, this coal transporting pipeline is provided with a corresponding solid particle equivalent atomic number measuring device, a corresponding gas-solid two-phase flow rate measuring device, a corresponding ash content measuring device, a corresponding volatile content measuring device and a corresponding moisture content measuring device Wherein, "this coal transporting pipeline being provided with a corresponding solid particle equivalent atomic number measuring device, a corresponding gas-solid two-phase flow rate measuring device, a corresponding ash content measuring device, a corresponding volatile content measuring device and a corresponding moisture content measuring device" refers to that the solid particle equivalent atomic number measuring device and the gas-solid two-phase flow rate measuring device are arranged on the coal transporting pipeline, while the ash content measuring device, the volatile content measuring device and the moisture content measuring device are arranged on the coal transporting path, either being arranged at the coal transporting pipeline, or being arranged not at the coal transporting pipeline but at other locations along the coal transporting path. "being arranged at the coal transporting pipeline" means the related devices can be positioned on the coal transporting pipeline or not positioned on the coal transporting pipeline, as mentioned above.

The production line may also include multiple coal transporting pipelines, for example, the cement production line includes a head coal transporting pipeline and a tail coal transporting pipeline.

In the present application, each of the coal transporting pipelines may be provided with a corresponding solid particle equivalent atomic number measuring device, a corresponding gas-solid two-phase flow rate measuring device, a corresponding ash content measuring device, a corresponding volatile content measuring device and a corresponding moisture content measuring device. This way is more suitable for multiple coal transporting pipelines using coals of different qualities.

In the present application, each of the coal transporting pipelines may be provided with a solid particle equivalent atomic number measuring device and a gas-solid two-phase flow rate measuring device; however, only one set of ash content measuring device, volatile content measuring device and moisture content measuring device is provided for a subgroup of coal transporting pipelines using coal powder of the same quality. The set of ash content measuring device, volatile content measuring device and moisture content measuring device is arranged on a common coal transporting path corresponding to the subgroup of coal transporting pipelines using coal powder of the same quality.

This way is more suitable for the situation that the multiple coal transporting pipelines have a subgroup of several pipelines using coal with the same quality. It only needs to measure the ash content, volatile content and moisture content for one of the coal transporting pipelines using coal of the same quality, and because coal of the same quality is used therein, the other coal transporting pipelines using coal with the same quality can adopt the same measurement result. Extremely, if all the coal transporting pipelines use coal of the same quality, it is only necessary to provide one solid particle equivalent atomic number measuring device, one gas-solid two-phase flow rate measuring device, one ash content measuring device, one volatile content measuring device and one moisture content measuring device for any one pipeline selected from the coal transporting pipelines.

The ash content measuring device, volatile content measuring device and moisture content measuring device being arranged on a coal transporting path corresponding to the subgroup of coal conveying pipelines using coal powder of the same quality refers to that the related devices may be arranged at the coal transporting pipeline, or can be arranged at other locations along the coal transporting path. The meaning of being arranged at the coal transporting pipeline is as mentioned above.

In the present application, preferably, the solid particle equivalent atomic number measuring device 1 and the gas-solid two-phase flow rate measuring device 2 are located upstream of the ash content measuring device 3, the volatile content measuring device 4 and the moisture content measuring device 4 in the coal transporting direction of the coal transporting pipeline 5 (the coal powder transporting direction is from bottom to top in FIG. 1). This aims to reduce the interference on the results of the online solid particle equivalent atomic number measuring device 1 and the online gas-solid two-phase flow rate measuring device 2 caused by change of coal powder distribution in the coal transporting pipeline 5 due to the sampling operation of the X-ray fluorescence spectral element analysis device 3 and the online volatile content and moisture content measuring device 4.

The coal transporting pipeline includes a horizontal part and a vertical part. Because of the effect of gravity, the horizontal part has uneven distribution of coal powder in the horizontal direction of the coal transporting pipeline. In the present application, the solid particle equivalent atomic number measuring device, the gas-solid two-phase flow rate measuring device, the ash content measuring device, the volatile content measuring device and the moisture content measuring device are located on a vertical part of the coal transporting pipeline, so that the measured data, especially the volume flow rate data, can be more accurate.

The afore-mentioned data acquisition and processing device 6 of the present application comprises a field computer server (including a calculation model and a software system), a data bus interconnecting the respective measuring devices, a data interface for uploading the measured results, etc. The data acquisition and processing device can also record and store the obtained statistical results; and if necessary, it can also output and upload the data obtained by the system.

The above described are preferred embodiments of the present application. It should be noted that, for a person with ordinary skill in the art, several improvements and refinements can also be made without departing from the described principles of the present application, and these improvements and refinements shall also be regarded as within the protection scope of the present application.

The invention claimed is:

1. A coal consumption online measuring system, characterized in that, the system comprises a solid particle equivalent atomic number measuring device, a gas-solid two-phase flow rate measuring device, an ash content measuring device, a volatile content measuring device and a moisture content measuring device, the solid particle equivalent atomic number measuring device and the gas-solid two-phase flow rate measuring device are installed on a coal transporting pipeline of a coal transporting path, the ash content measuring device, the volatile content measuring device and the moisture content measuring device are arranged on the coal transporting path, the solid particle equivalent atomic number measuring device, the gas-solid two-phase flow rate measuring device, the ash content measuring device, the volatile content measuring device and the moisture content measuring device are all connected to a data acquisition and processing device, wherein:

the solid particle equivalent atomic number measuring device and the gas-solid two-phase flow rate measuring device are configured to measure a real-time density and a real-time volume flow rate of coal powder in the coal transporting pipeline, the ash content measuring device, the volatile content measuring device and the moisture content measuring device are configured to measure a real-time ash content, a real-time moisture content and a real-time volatile content of coal powder in the coal transporting path, the real-time ash content includes a total content of ash, the element composition of the ash and the contents of the respective elements in the ash;

the data acquisition and processing device is configured to calculate a matrix characteristic of the coal powder according to one or more of the measured real-time density, real-time ash content, real-time moisture content and real-time volatile content, and iteratively correct one or more of the measured real-time density, real-time ash content, real-time moisture content and real-time volatile content according to the calculated matrix characteristic of the coal powder;

the data acquisition and processing device is configured to calculate a real-time mass flow rate according to the iteratively-corrected real-time density and the real-time volume flow rate, and calculate a real-time calorific value of the coal powder according to the iteratively-corrected real-time ash content, real-time moisture content and real-time volatile content;

the data acquisition and processing device is configured to calculate a real-time energy of the coal powder according to the real-time mass flow rate and the real-time calorific value, and perform time integration of the real-time energy to determine a coal consumption within a prescribed time period.

2. The coal consumption online measuring system according to claim 1, characterized in that, the solid particle equivalent atomic number measuring device comprises a radiation source device, a detection device and a first analysis and communication component; the radiation source device is configured to emit radiation rays towards the coal powder in the coal transporting pipeline, and the detection device is configured to receive a signal after the radiation rays penetrate the coal powder or are reflected from the coal powder, the first analysis and communication component is configured to analyze and obtain an equivalent atomic number of the coal powder in the coal transporting pipeline, calculate the real-time density according to the equivalent atomic number and send the real-time density to the data acquisition and processing device; the radiation source device is an X-ray source or a γ-ray source.

3. The coal consumption online measuring system according to claim 1, characterized in that, the gas-solid two-phase flow rate measuring device comprises at least one set of microwave emitting unit and microwave receiving unit distributed on the coal transporting pipeline, the microwave emitting unit and the microwave receiving unit are both connected to a second analysis and communication component; the microwave emitting unit is configured to emit microwaves and the microwave receiving unit is configured to receive the microwaves reflected by the coal powder in the coal transporting pipeline, the second analysis and communication component is configured to analyze and obtain the real-time volume flow rate in the coal transporting pipeline and send the real-time volume flow rate to the data acquisition and processing device.

4. The coal consumption online measuring system according to claim 1, characterized in that, the ash content measuring device is arranged on the coal transporting pipeline, the ash content measuring device is an X-ray fluorescent spectral element analysis device, and the X-ray fluorescent spectral element analysis device comprises an X-ray generating device, an X-ray detector component, an optical path device, a first sampling device and a third analysis and communication component; the first sampling device is configured to grab a first coal powder sample from inside the coal transporting pipeline and transport the first coal powder sample to a working area of the X-ray generating device, the X-ray generating device is configured to emit X-rays which pass through the optical path device and irradiate the first coal powder sample to produce reflected X-rays with information on the elements in the coal powder, the X-ray detector component is configured to receive the reflected X-rays and the third analysis and communication component is configured to analyze and process the reflected X-rays to determine the total content of ash in the first coal powder sample, the element composition of the ash and the contents of the respective elements in the ash and then send the determined parameters to the data acquisition and processing device.

5. The coal consumption online measuring system according to claim 4, characterized in that, the volatile content measuring device and the moisture content measuring device are arranged on the coal transporting pipeline, the volatile content measuring device and the moisture content measuring device are integrated in one structure which comprises a light source component, a detector component, a second sampling device and a fourth analysis and communication component; the second sampling device is configured to grab a second coal powder sample from the coal transporting pipeline and transport the second coal powder sample to a working area of the light source component, the light source component is configured to emit light to illuminate the second coal powder sample to produce reflected or transmitted light with information on the volatile content and moisture content of the coal powder, the detection component is configured to collect the reflected or transmitted light and the fourth analysis and communication component is configured to analyze and process the reflected or transmitted light to determine the volatile content and moisture content of the second coal powder sample and then send the determined parameters to the data acquisition and processing device; the light source component is an infrared light source or a Raman light source.

6. The coal consumption online measuring system according to claim 5, characterized in that, the first sampling device and the second sampling device are the same sampling device, the first coal powder sample and the second coal powder sample are the same sample.

7. The coal consumption online measuring system according to claim 1, characterized in that, the system is used in a production line of a coal consumption plant, the production line includes one or more coal transporting pipelines, wherein, when multiple coal transporting pipelines are included:
- each of the coal transporting pipelines is provided with a corresponding solid particle equivalent atomic number measuring device, a corresponding gas-solid two-phase flow rate measuring device, a corresponding ash content measuring device, a corresponding volatile content measuring device and a corresponding moisture content measuring device; or
- each of the coal transporting pipelines is provided with a solid particle equivalent atomic number measuring device and a gas-solid two-phase flow rate measuring device, and one set of ash content measuring device, volatile content measuring device and moisture content measuring device is provided for a subgroup of coal transporting pipelines using coal powder of the same quality among the multiple coal transporting pipelines, and the set of ash content measuring device, volatile content measuring device and moisture content measuring device is arranged on a common coal transporting path corresponding to the subgroup of coal transporting pipelines using coal powder of the same quality.

8. The coal consumption online measuring system according to claim 7, characterized in that, the solid particle equivalent atomic number measuring device and the gas-solid two-phase flow rate measuring device are located upstream of the ash content measuring device, the volatile content measuring device and the moisture content measuring device in the coal transporting direction of the coal transporting pipeline.

9. The coal consumption online measuring system according to claim 8, characterized in that, the solid particle equivalent atomic number measuring device, the gas-solid two-phase flow rate measuring device, the ash content measuring device, the volatile content measuring device and the moisture content measuring device are located on a vertical part of the coal transporting pipeline.

\* \* \* \* \*